(12) United States Patent
Thomas-Tikhonenko et al.

(10) Patent No.: US 10,751,356 B2
(45) Date of Patent: Aug. 25, 2020

(54) COMPOSITIONS AND METHODS FOR TRANSIENT UP-REGULATION OF MYC IN B-CELL LYMPHOMAS FOR ENHANCING P53 INDEPENDENT APOPTOTIC RESPONSES TO CHEMOTHERAPY

(71) Applicant: THE CHILDREN'S HOSPITAL OF PHILADELPHIA, Philadelphia, PA (US)

(72) Inventors: Andrei Thomas-Tikhonenko, Philadelphia, PA (US); Elena Sotillo-Pineiro, Ardmore, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 346 days.

(21) Appl. No.: 14/875,094

(22) Filed: Oct. 5, 2015

(65) Prior Publication Data
US 2016/0095873 A1    Apr. 7, 2016

Related U.S. Application Data

(63) Continuation-in-part of application No. PCT/US2014/033200, filed on Apr. 7, 2014.

(60) Provisional application No. 61/809,131, filed on Apr. 5, 2013.

(51) Int. Cl.
| | | |
|---|---|---|
| *A61K 31/704* | (2006.01) | |
| *A61K 31/506* | (2006.01) | |
| *A61K 31/426* | (2006.01) | |
| *A61K 45/06* | (2006.01) | |
| *A61K 31/404* | (2006.01) | |
| *A61K 33/14* | (2006.01) | |

(52) U.S. Cl.
CPC .......... *A61K 31/704* (2013.01); *A61K 31/404* (2013.01); *A61K 31/426* (2013.01); *A61K 31/506* (2013.01); *A61K 33/14* (2013.01); *A61K 45/06* (2013.01)

(58) Field of Classification Search
CPC .................................................. A61K 31/704
USPC ......................................................... 435/7.23
See application file for complete search history.

(56) References Cited

U.S. PATENT DOCUMENTS

| | | |
|---|---|---|
| 7,732,436 B2 | 6/2010 | Tepe |
| 2008/0139620 A1 | 6/2008 | Wyatt et al. |
| 2009/0041863 A1 | 2/2009 | Hallahan |
| 2009/0304663 A1 | 12/2009 | Kypta |
| 2010/0021420 A1 | 1/2010 | Lyons et al. |
| 2011/0003799 A1 | 1/2011 | Bedini et al. |

FOREIGN PATENT DOCUMENTS

WO    2011149762 A2    12/2011

OTHER PUBLICATIONS

Musolino et al (Cancer, 2005, 103(10): 2109-2117).*
Nkrumah et al (Cancer, 1976, 37: 671-676).*
Malempati et al (Leukemia, 2006, 20(9): 1572-1581).*
Hermeking et al (Science, 1994, 265(30): 2091-2093).*
Richter-Larrea et al (Blood, 2010, 116(14): 2531-2542).*
Kuttler et al (Oncogene, 2011, 20: 6084-6094).*
Molyneux et al (The Lancet, 2012, 379: 1234-1244).*
Hickman (Cancer Metastasis Rev, 1992, 11(2): Abstract).*
Rottmann et al (PNAS, 2005, 102(42): 15195-15200).*
Baritaki et al (Mol Cancer Ther, 2007, 6(4): 1387-1399).*
Amaravadi et al., Autophagy inhibition enhances therapy-induced apoptosis in a Myc-induced model of lymphoma. J Clin Inv. 2007, 117(2):326-36.
Mussman et al., Inhibition of GSK3 Promotes Replication and Survival of Pancreatic Beta Cells. J Biol Chem. 2007, 282(16):12030-7.
Smith-Sørensen et al., Functional analysis of Burkitt's lymphoma mutant c-Myc proteins. J Biol Chem. 1996, 271(10):5513-8.
Sotillo et al., Myc overexpression brings out unexpected antiapoptotic effectsof miR-34a. Oncogene. 2011, 30(22):2587-94.
Stuckey et al., TRAIL on trial: preclinical advances in cancer therapy. Trends Mol Med. 2013, 19(11):685-94.
Yu et al., p53 status dictates responses of B lymphomas to monotherapy with proteasome inhibitors. Blood. 2007, 109(11): 4936-43.
International Search Report and Written Opinion in PCT/US2011/037179, dated Feb. 24, 2012.

* cited by examiner

*Primary Examiner* — Sean E Aeder
(74) *Attorney, Agent, or Firm* — Howson & Howson LLP; Kathleen D. Rigaut

(57) ABSTRACT

Compositions and methods useful for the treatment of cancer, particularly lymphoma, are disclosed.

6 Claims, 15 Drawing Sheets

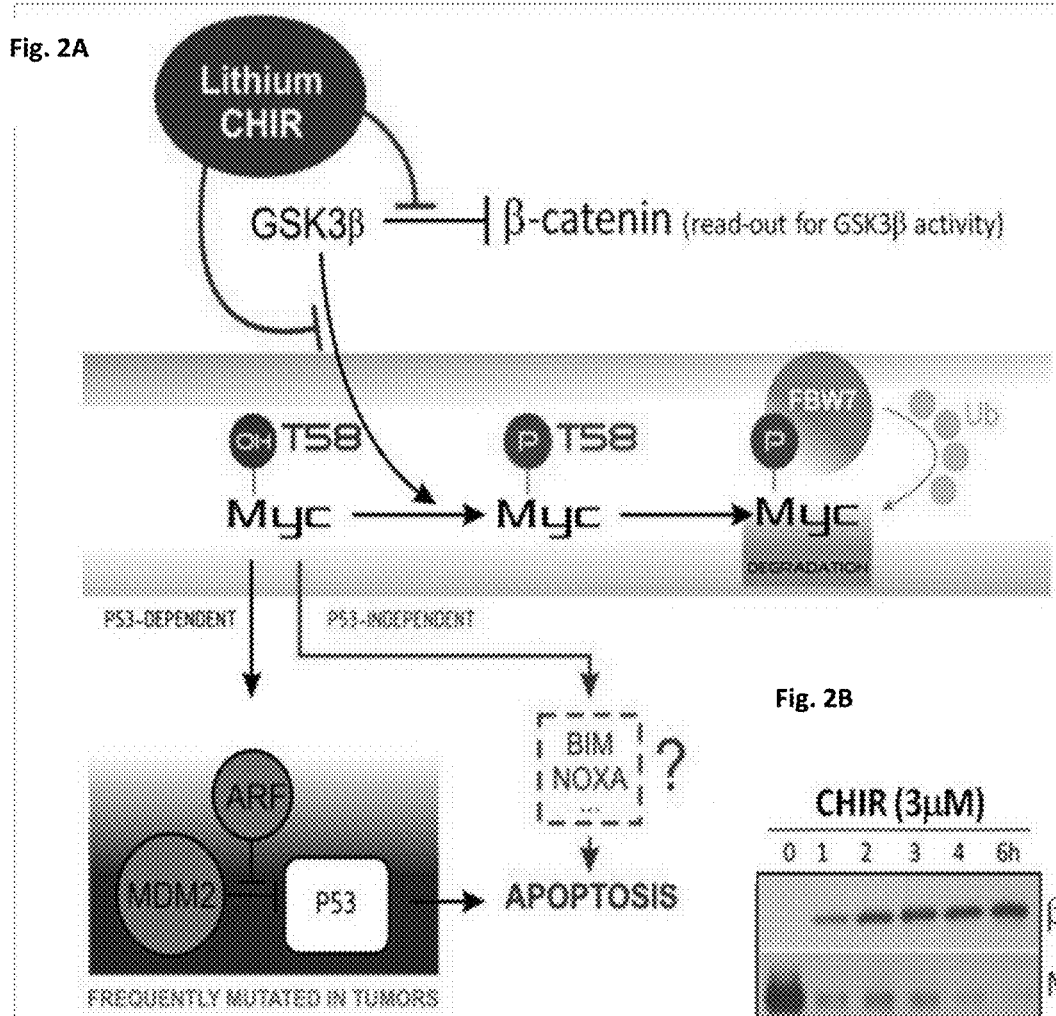
Fig. 2A
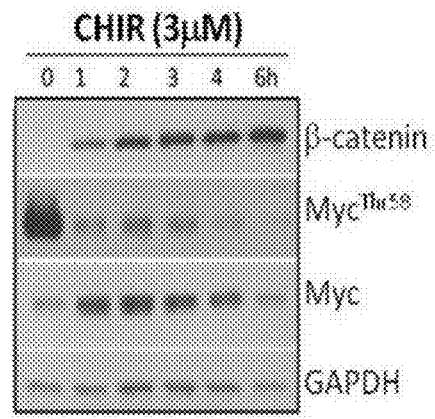
Fig. 2B
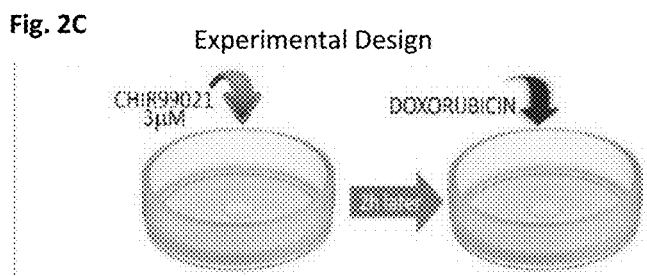
Fig. 2C Experimental Design

COMPOSITIONS AND METHODS FOR TRANSIENT UP-REGULATION OF MYC IN B-CELL LYMPHOMAS FOR ENHANCING P53 INDEPENDENT APOPTOTIC RESPONSES TO CHEMOTHERAPY

This application is a § 365 application of PCT/US2014/33200 filed Apr. 7, 2014 which in turn claims priority to U.S. Provisional Application No. 61/809,131 filed Apr. 5, 2013, the entire contents of each being incorporated herein by reference as though set forth in full.

FIELD OF THE INVENTION

This invention relates to the fields of oncology and chemotherapy. More specifically, the invention provides compositions useful to stabilize Myc protein thereby enhancing apoptotic cell death in targeted malignant cells.

BACKGROUND OF THE INVENTION

Several publications and patent documents are cited throughout the specification in order to describe the state of the art to which this invention pertains. Each of these citations is incorporated herein by reference as though set forth in full.

Myc protein is a transcription factor that activates expression of many genes through binding on consensus sequences (Enhancer Box sequences (E-boxes)) and recruiting histone acetyltransferases (HATs). It can also act as a transcriptional repressor. By binding Miz-1 transcription factor and displacing the p300 co-activator, it inhibits expression of Miz-1 target genes. In addition, myc has a direct role in the control of DNA replication. Myc is activated upon various mitogenic signals such as Wnt, Shh and EGF (via the MAPK/ERK pathway). By modifying the expression of its target genes, Myc activation results in numerous biological effects. The first to be discovered was its capability to drive cell proliferation (upregulates cyclins, downregulates p21), but it also plays a very important role in regulating cell growth (upregulates ribosomal RNA and proteins), apoptosis (downregulates Bcl-2), differentiation and stem cell self-renewal. Myc is a very strong proto-oncogene and it is very often found to be upregulated in many types of cancers. Myc overexpression stimulates gene amplification presumably through DNA over-replication.

Myc oncogene dysregulation has been observed in a number of different malignancies. Clearly agents which impact the action of this oncoprotein should have efficacy for the treatment of cancer.

SUMMARY OF THE INVENTION

In accordance with the present invention, a method is provided which enhances cancer cell apoptosis in a p53 independent fashion, thereby reducing cancer cell or tumor burden in a patient in need thereof. An exemplary method entails administration of an effective amount of an glycogen synthase kinase 3β (GSK3β) inhibitor in combination with an apoptosis inducing chemotherapeutic or anti-cancer agent, said inhibitor being effective to stabilize myc, thereby enhancing the apoptosis inducing action of the chemotherapeutic or anti-cancer agent. In one embodiment, the agents act synergistically to kill cancer cells.

In a preferred embodiment, the cancer is a B cell lymphoma, the anti-cancer agent is doxorubicin and the GSK3β inhibitor is selected from the group consisting of CT99021 ((6-{2-[4-(2,4-dichlorophenyl)-5-(4-methyl-1H-imidazol-2-yl)-pyrimidin-2-ylamino]ethyl-amino}nicotinonitrile), lithium chloride, 6-bromoindirubin-3-oxime, 1-azakenpaullone, AR-A014418, and SB216763. In a particularly preferred embodiment of the method the GSK3β inhibitor is ((6-{2-[4-(2,4-dichlorophenyl)-5-(4-methyl-1H-imidazol-2-yl)-pyrimidin-2-ylamino]ethyl-amino}nicotinonitrile).

In yet another aspect, a method for identifying those patients that will benefit from the combination therapy described above is provided. An exemplary method entails isolating a biological sample from a patient and assessing the patient for the presence or absence of myc mutation at position threonine 58, and treating patients with the therapy described above when the mutation is absent. In another aspect of the method, patients identified as possessing the mutation will be treated with TRAIL and a GSK-3 inhibitor in order to induce cancer cell death.

BRIEF DESCRIPTION OF THE DRAWINGS

FIG. 1A: Experimental design with p53 wt mice; FIG. 1B: Western blot; FIG. 1C: Experimental design with p53 null mice.

FIGS. 2A-2C: Model of Myc regulation and proposed strategy to increase p53-independent apoptosis. FIG. 2A: Read out for GSK3β activity; FIG. 2B: Northern blot; FIG. 2C: Experimental design.

FIG. 6A: Ramos cells exposed to doxorubicin; FIG. 6B: Caspase 3/7 Activity; FIG. 6C: Ramos cells exposed to vincristine.

(FIG. 9A)

Immunoblotting with antibodies to detect cleavage of PARP and caspase-8, as well as Myc, beta-catenin and loading controls Tutbulin, Actin and GAPDH. (FIG. 9B) Caspase-3/7 activity were measured using the bioluminescent-based Caspase-3/7 Glo Kit (Promega). Fold increase in caspase activities relative to untreated cells, are shown for cells treated with TRAIL alone (light grey bars) or with TRAIL and CHIR-99021 (dark grey bars).

Figure 1A:
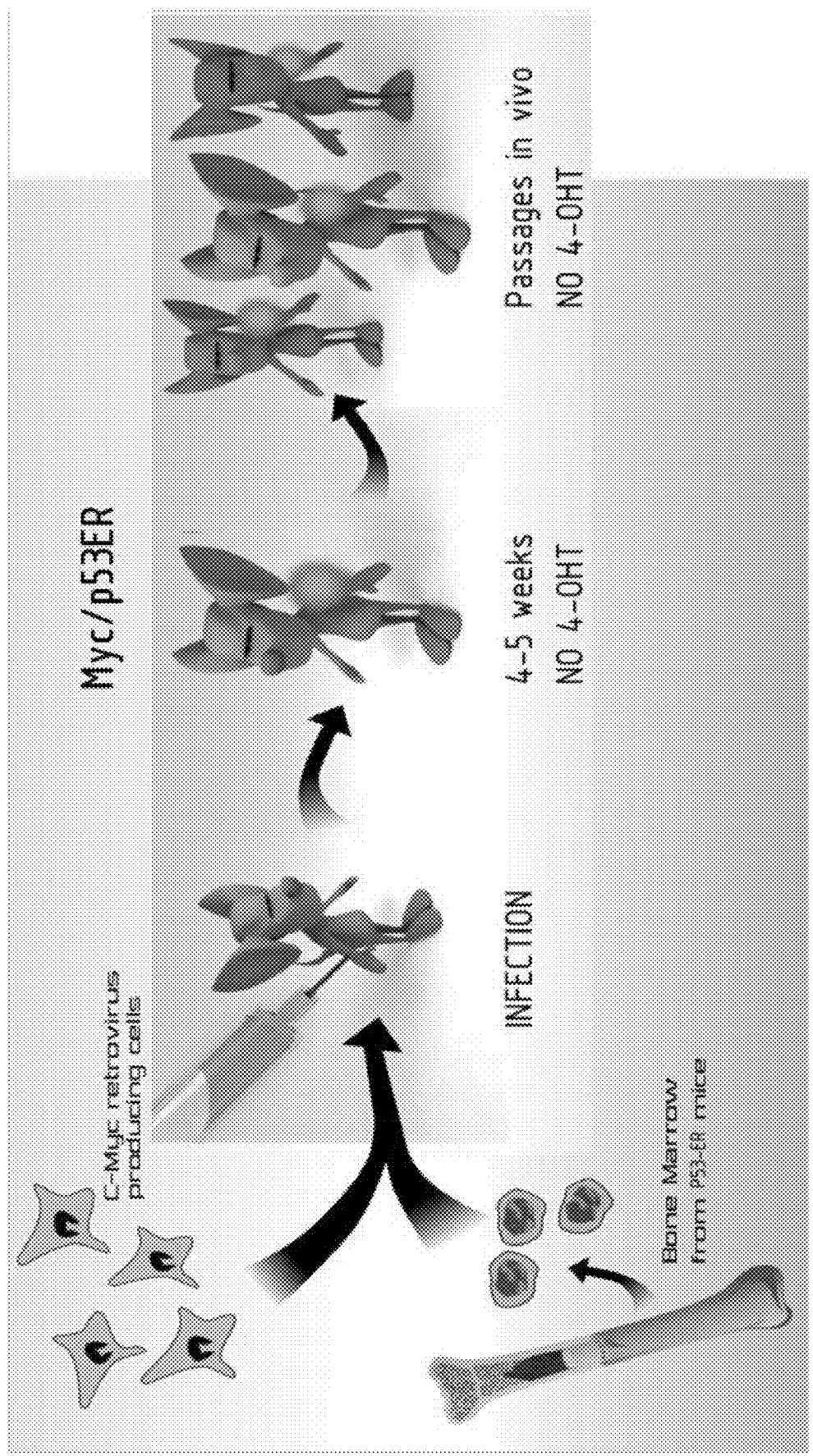
FIGS. 1A-1C: Non-transgenic B-lymphoma models with inducible p53/Myc to study p53-independent Myc-dependent cell death.
Figure 1B:
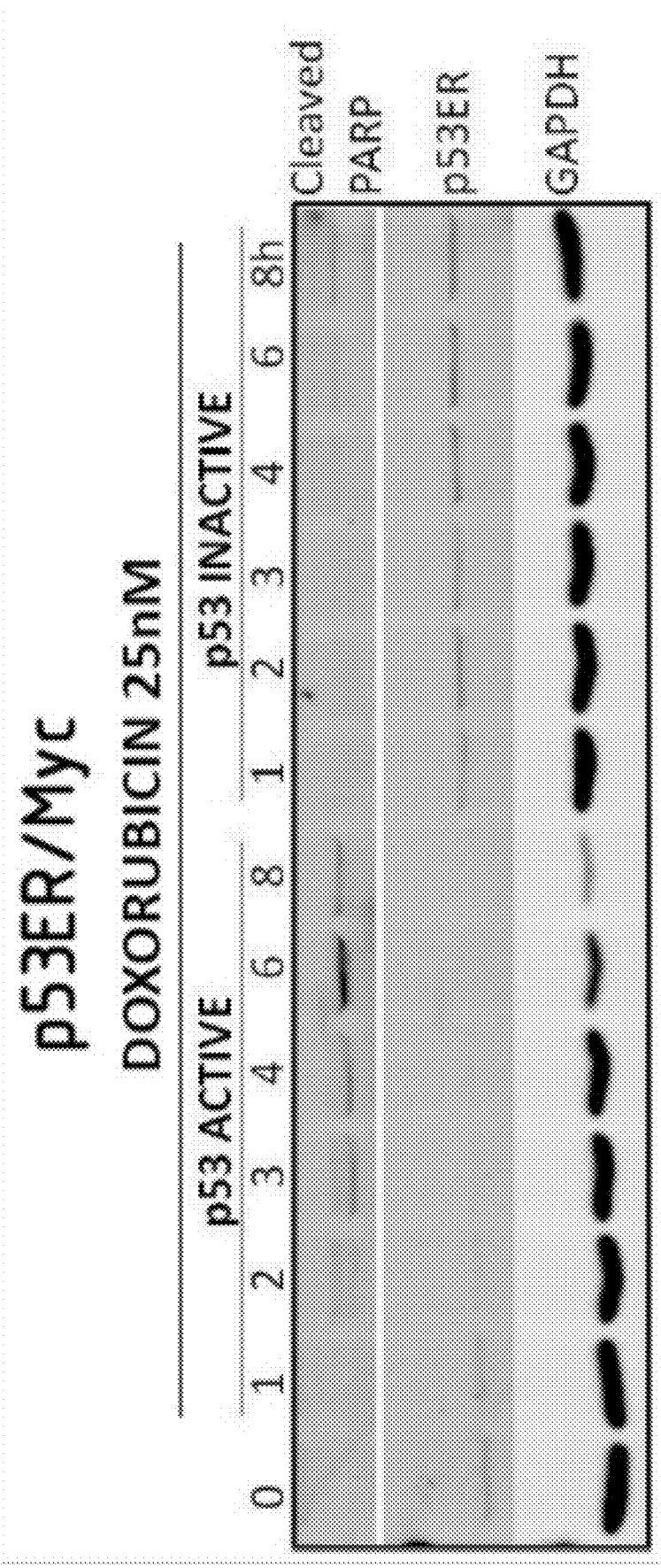
Figure 1C:
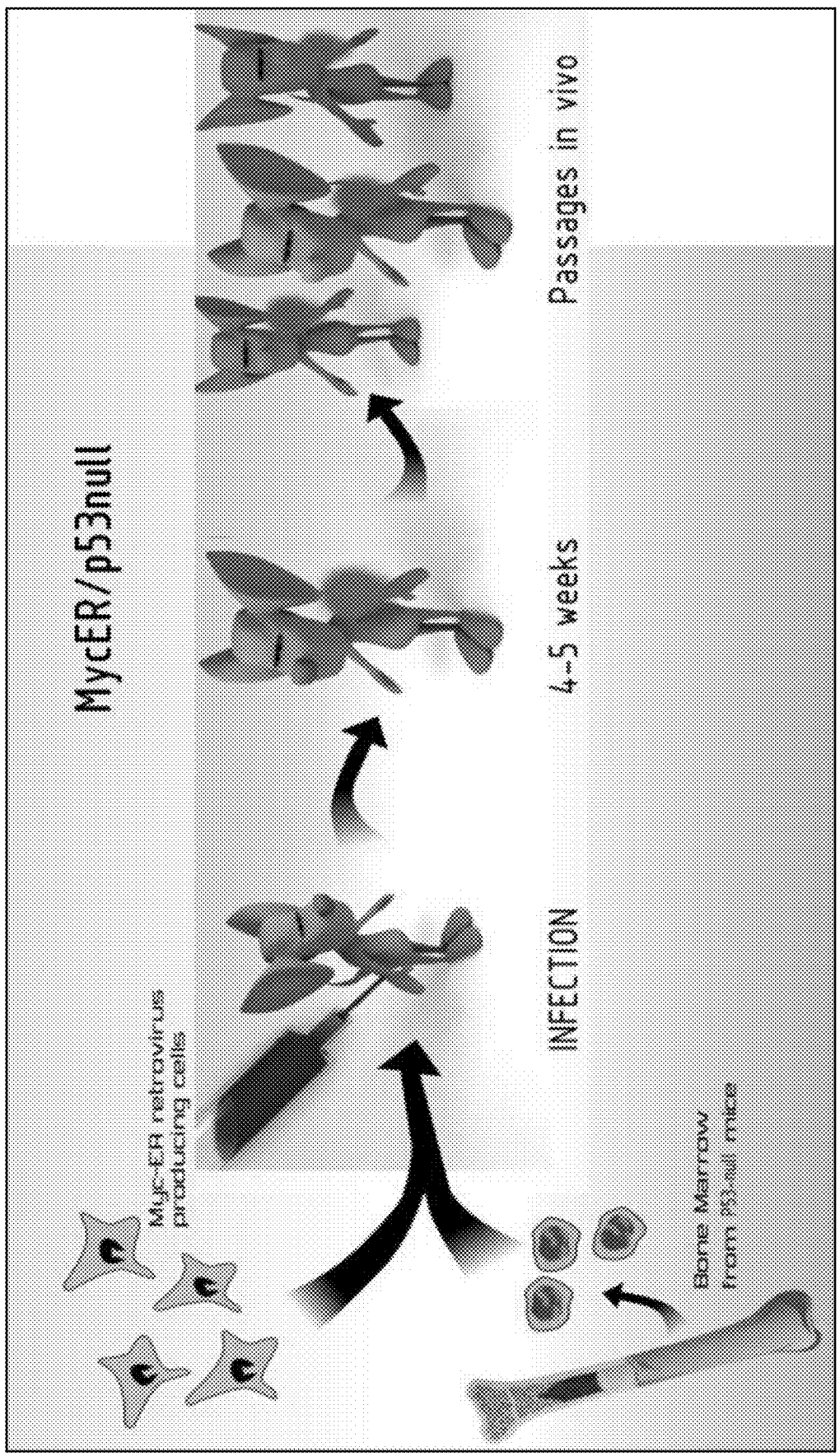
Figure 1D:
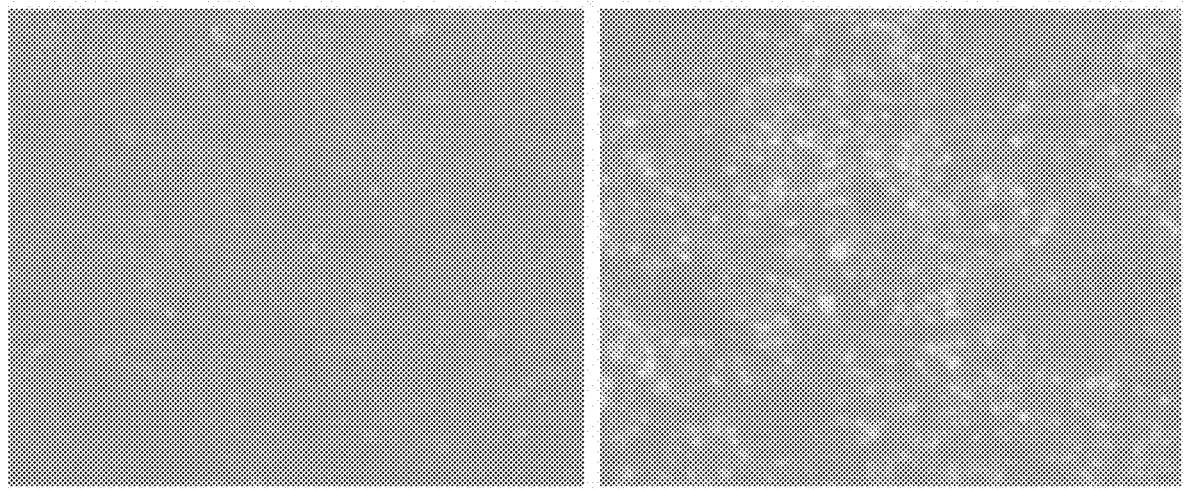
FIG. 1D: Tunel Assay.

DETAILED DESCRIPTION OF THE INVENTION c-MYC oncogene deregulation is a common trait in human cancers, with programmed cell death (or apoptosis) being among Myc-regulated events. Myc is well-known to induce apoptosis in a p53-dependent manner, via the Myc→ARF-|MDM2-|p53 pathway. We had previously shown that this pathway can be exploited to increase sensitivity to anti-cancer drugs.

In accordance with the present invention, we have identified therapeutic combinations useful for increasing cell killing in Burkitt's lymphoma cells and other cancer cells. Surprisingly, we have found that inhibition of GSK3β transiently increases Myc levels and sensitizes targeted cancer cells to anti-cancer agents.

I. Definitions

A "pharmaceutical candidate" or "drug candidate" is a compound believed to have therapeutic potential which will be assessed for efficacy.

The "screening" of a pharmaceutical candidate refers to conducting an assay that is capable of evaluating the efficacy and/or specificity of the candidate. In this context, "efficacy" refers to the ability of the candidate to effect the cell or organism it is administered to in a beneficial way: for example, the limitation of the pathology of cancerous cells.

A "cell line" or "cell culture" denotes higher eukaryotic cells grown or maintained in vitro. It is understood that the descendants of a cell may not be completely identical (either morphologically, genotypically, or phenotypically) to the parent cell. Cells described as "uncultured" are obtained directly from a living organism, and have been maintained for a limited amount of time away from the organism: not long enough or under conditions for the cells to undergo substantial replication.

A "host cell" is a cell which has been transformed, or is capable of being transformed, by administration of an exogenous polynucleotide.

The terms "cancerous cell" or "cancer cell", used either in the singular or plural form, refer to cells that have undergone a malignant transformation that makes them pathological to the host organism. Malignant transformation is a single- or multi-step process, which involves in part an alteration in the genetic makeup of the cell and/or the expression profile. Malignant transformation may occur either spontaneously, or via an event or combination of events such as drug or chemical treatment, radiation, fusion with other cells, viral infection, or activation or inactivation of particular genes. Malignant transformation may occur in vivo or in vitro, and can if necessary be experimentally induced.

A frequent feature of cancer cells is the tendency to grow in a manner that is uncontrollable by the host, but the pathology associated with a particular cancer cell may take another form. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

The "pathology" caused by a cancer cell within a host is anything that compromises the well-being or normal physiology of the host. This may involve (but is not limited to) abnormal or uncontrollable growth of the cell, metastasis, release of cytokines or other secretory products at an inappropriate level, manifestation of a function inappropriate for its physiological milieu, interference with the normal function of neighboring cells, aggravation or suppression of an inflammatory or immunological response, or the harboring of undesirable chemical agents or invasive organisms.

"Treatment" of an individual or a cell is any type of intervention in an attempt to alter the natural course of the individual or cell. For example, treatment of an individual may be undertaken to decrease or limit the pathology caused by a cancer cell harbored in the individual. Treatment includes (but is not limited to) administration of a composition, such as a pharmaceutical composition, and may be performed either prophylactically, or subsequent to the initiation of a pathologic event or contact with an etiologic agent.

"Apoptosis" is a process of programmed cell death (PCD) that may occur in multicellular organisms. Biochemical events lead to characteristic cell changes (morphology) and death. These changes include blebbing, cell shrinkage, nuclear fragmentation, chromatin condensation, and chromosomal DNA fragmentation. In contrast to necrosis, which is a form of traumatic cell death that results from acute cellular injury, apoptosis generally confers advantages during an organism's life cycle.

The term "cancer" as used herein includes, without limitation, B cell lymphoma, cancers of the prostate, colorectum, pancreas, cervix, stomach, endometrium, brain, liver, bladder, ovary, testis, head, neck, skin (including melanoma and basal carcinoma), mesothelial lining, white blood cell (including leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

A "control cell" is an alternative source of cells or an alternative cell line used in an experiment for comparison purposes. Where the purpose of the experiment is to establish a base line for gene copy number or expression level, it is generally preferable to use a control cell that is not a cancer cell.

It is understood that a "clinical sample" encompasses a variety of sample types obtained from a subject and useful in an in vitro procedure, such as a diagnostic test. The definition encompasses solid tissue samples obtained as a surgical removal, a pathology specimen, or a biopsy specimen, tissue cultures or cells derived therefrom and the progeny thereof, and sections or smears prepared from any of these sources. Non-limiting examples are samples obtained from breast tissue, lymph nodes, and tumors. The definition also encompasses blood, spinal fluid, and other liquid sample of biologic origin, and may refer to either the cells or cell fragments suspended therein, or to the liquid medium and its solutes.

The term "relative amount" is used where a comparison is made between a test measurement and a control measurement. Thus, the relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

A "differential" result is generally obtained from an assay in which a comparison is made between the findings of two different assay samples, such as a cancerous cell line and a control cell line. Thus, for example, "differential expression" is observed when the level of expression of a particular gene is higher in one cell than another. "Differential display" refers to a display of a component, particularly RNA, from different cells to determine if there is a difference in the level of the component amongst different cells. Differential display of RNA is conducted, for example, by selective production and display of cDNA corresponding thereto.

The practice of the present invention will employ, unless otherwise indicated, conventional techniques of molecular biology, microbiology, recombinant DNA, and immunology, which are within the skill of the art. Such techniques are explained fully in the literature. See, for example, "Molecular Cloning: A Laboratory Manual", Second Edition (Sambrook, Fritsch & Maniatis, 1989), "Oligonucleotide Synthesis" (M. J. Gait, ed., 1984), "Animal Cell Culture" (R. I. Freshney, ed., 1987); the series "Methods in Enzymology" (Academic Press, Inc.); "Handbook of Experimental Immunology" (D. M. Weir & C. C. Blackwell, Eds.), "Gene Transfer Vectors for Mammalian Cells" (J. M. Miller & M. P. Calos, eds., 1987), "Current Protocols in Molecular Biology" (F. M. Ausubel et al., eds., 1987); and "Current Protocols in Immunology" (J. E. Coligan et al., eds., 1991).

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

A "carrier" refers to, for example, a diluent, adjuvant, excipient, auxiliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

Chemotherapeutic agents are compounds that exhibit anticancer activity and/or are detrimental to a cell (e.g., a toxin). Suitable chemotherapeutic agents for use in the methods disclosed herein include, but are not limited to: toxins (e.g., saporin, ricin, abrin, ethidium bromide, diptheria toxin, *Pseudomonas* exotoxin, and others listed above); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). In a particular embodiment, the chemotherapeutic agent is selected from the group consisting of: placitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

Molecular modeling should facilitate the identification of specific organic molecules with capacity to bind to the active site of myc protein based on conformation or key amino acid residues required for function. A combinatorial chemistry approach can be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, NH), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The present invention further provides "compositions" in biological compatible solution, pharmaceutically acceptable excipient, carrier, buffer, stabilizer or other materials well known to those skilled in the art, comprising the nucleic acids, polypeptides, vectors or antibodies of the invention. A biologically compatible solution is a solution in which the small molecule of the invention is maintained in an active form, e.g. in a form able to effect a biological activity. Generally, such a biologically compatible solution will be an aqueous buffer, e.g. Tris, phosphate, or HEPES buffer, containing salt ions. Usually the concentration of salt ions will be similar to physiological levels. Biologically compatible solutions may include stabilizing agents and preservatives.

Such compositions may be formulated for administration by topical, oral, parenteral, intranasal, subcutaneous, and intraocular routes. Parenteral administration is meant to include intravenous injection, intramuscular injection, intraarterial injection or infusion techniques. The compositions may be administered parenterally in dosage unit formulations containing standard well known non-toxic physiologically acceptable carriers, adjuvants and vehicles as desired. The preferred sterile injectable preparations may be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or a mixture or such salts), Ringers solution, dextrose, water, sterile water, glycol, ethanol, and combinations thereof. 1,3-butanediol and sterile fixed oils are conveniently employed as solvents or suspending media. Any bland fixed oil may be employed including synthetic mono- or di-glycerides. Fatty acids such as oleic acid also find use in the preparation of injectables.

The present invention provides "methods of treatment" which comprise the administration to a human or other animal of an effective amount of a composition of the invention.

Effective amounts vary, depending on the age, type and severity of the condition to be treated, body weight, desired duration of treatment, method of administration, and other parameters. Effective amounts are determined by a physician or other qualified medical professional.

The following example is provided to illustrate certain embodiments of the invention. It is not intended to limit the invention in any way.

Example I

Figure 3A:
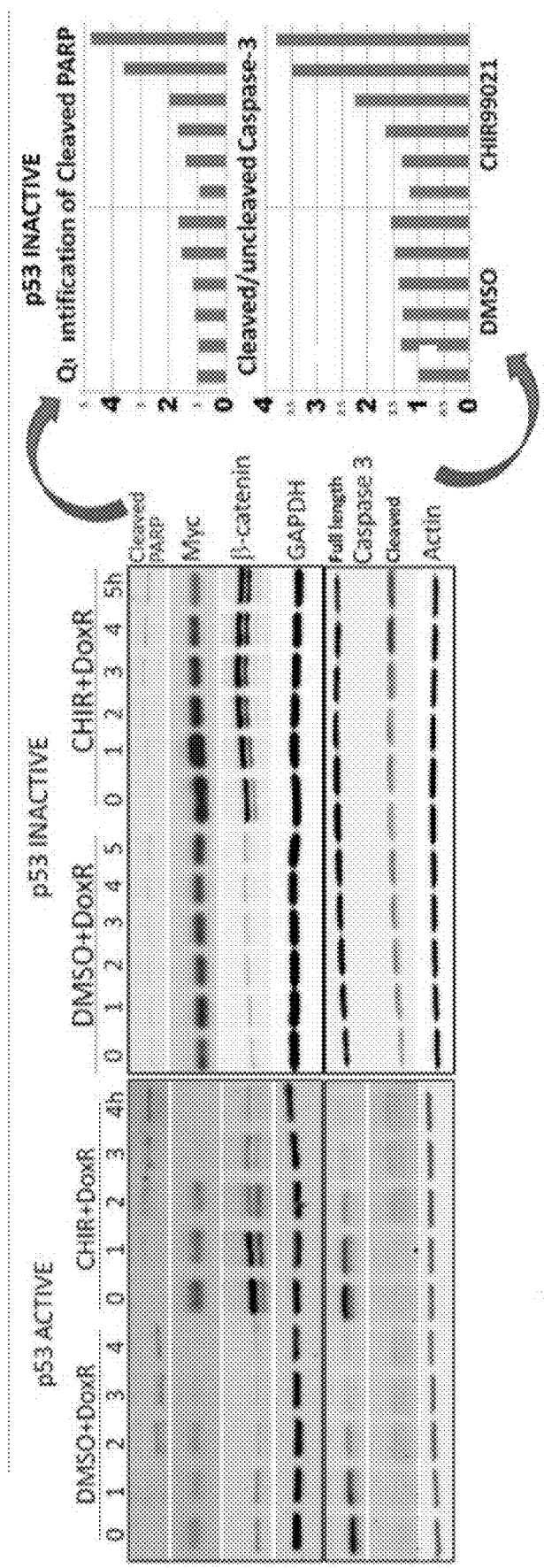
FIGS. 3A-3B: In the absence of p53, GSK3β inhibition=>Myc stabilization enhances apoptotic response to Doxorubicin (FIG. 3A) by increasing levels of pro-apoptotic genes (FIG. 3B).
Figure 3B:
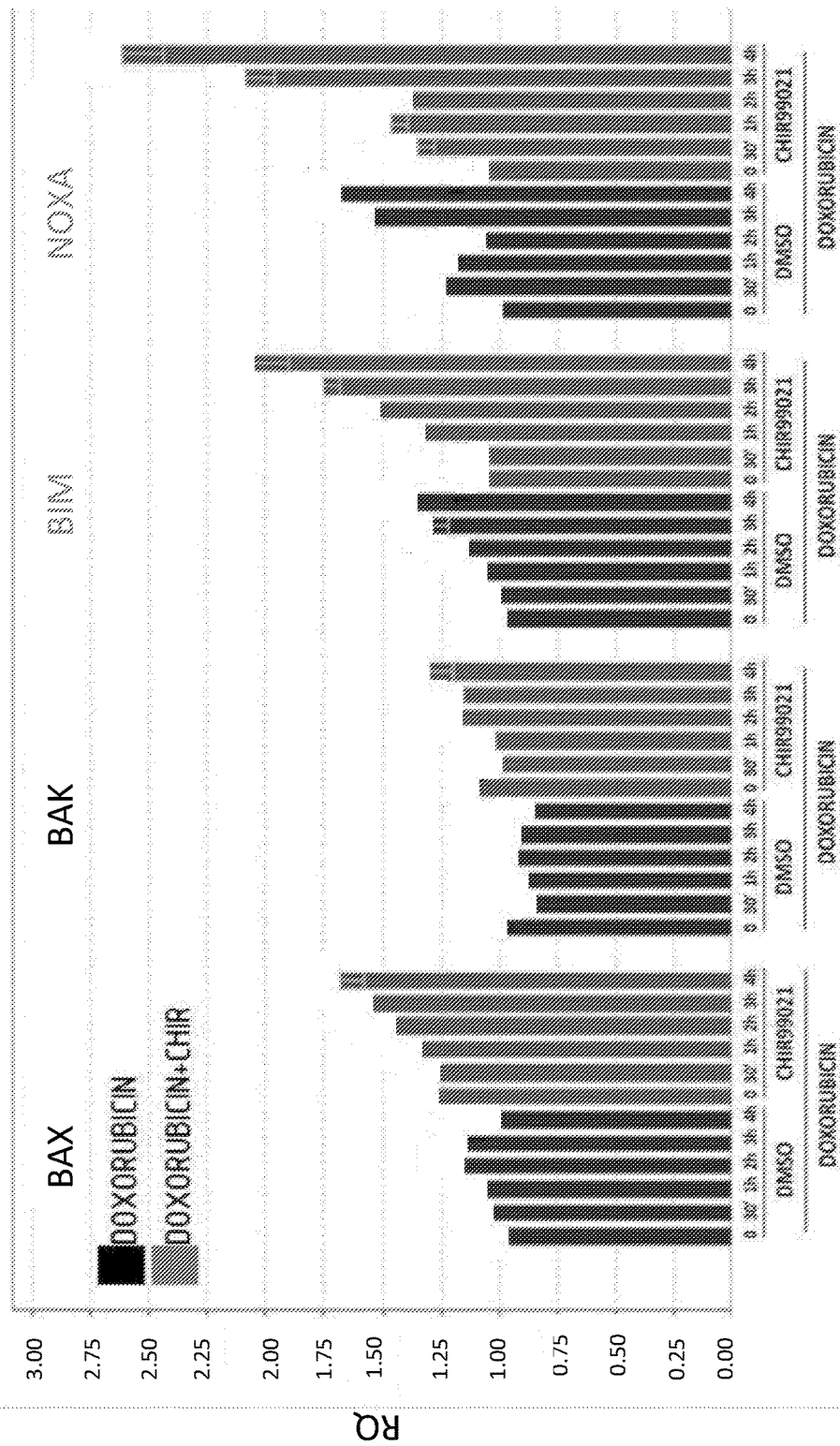
Figure 4A:
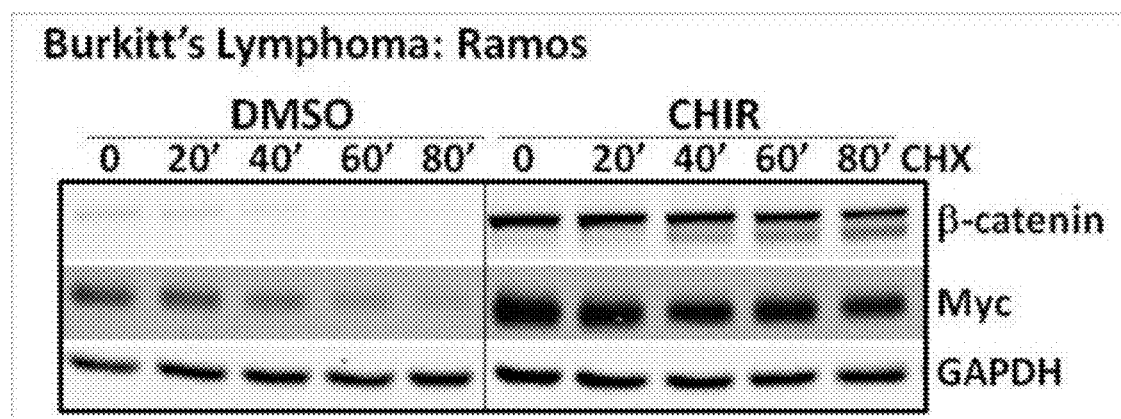
FIGS. 4A-4F: Prevention of MycThr58 phosphorylation by GSK3b prolongs Myc half-life in a variety of human B cell lymphoma cell lines. Burkitt's lymphoma: Ramos FIGS. 4A and 4D; Human lymphoid: P493-6 FIGS. 4B and 4E; Diffuse large B cell lymphoma: OCI-LY3 FIGS. 4C and 4F.
Figure 4B:
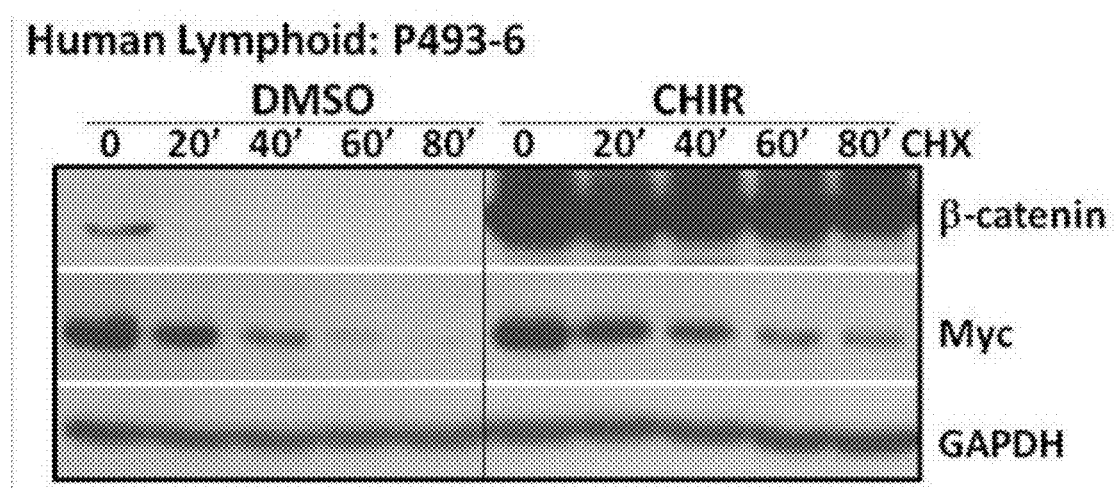
Figure 4C:
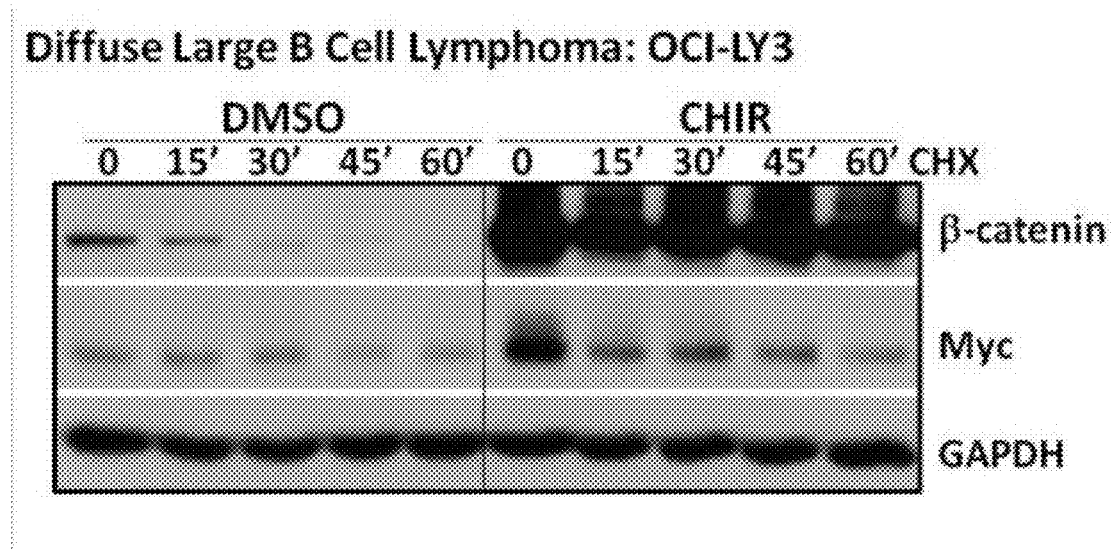
Figure 4D:
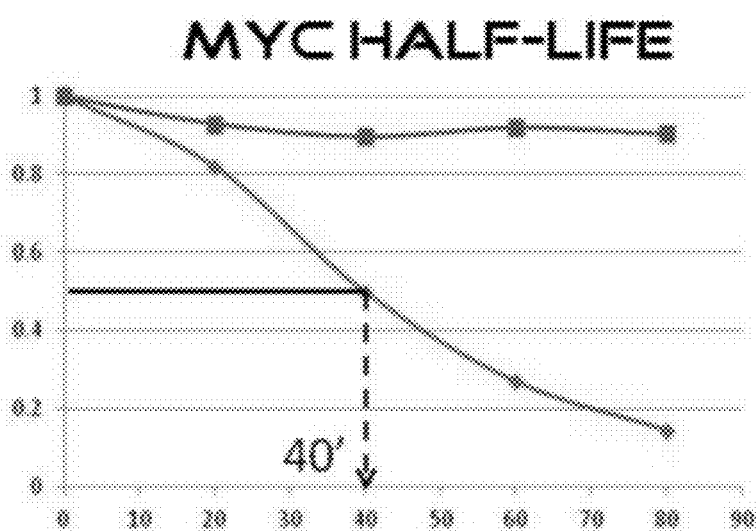
Figure 4E:
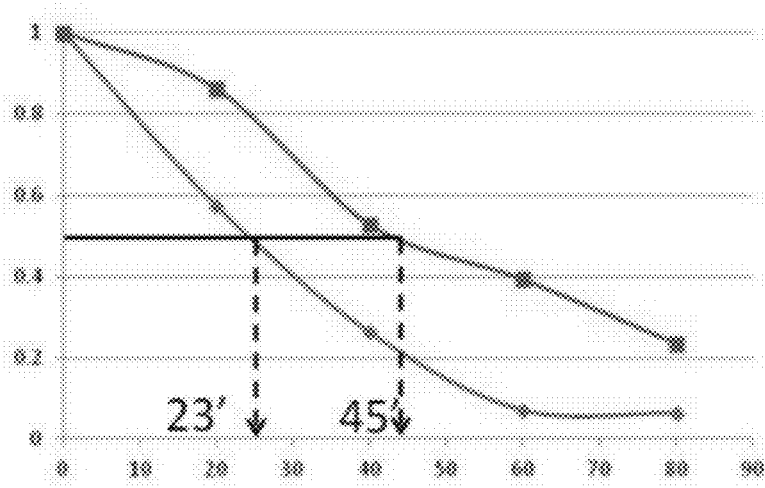
Figure 4F:
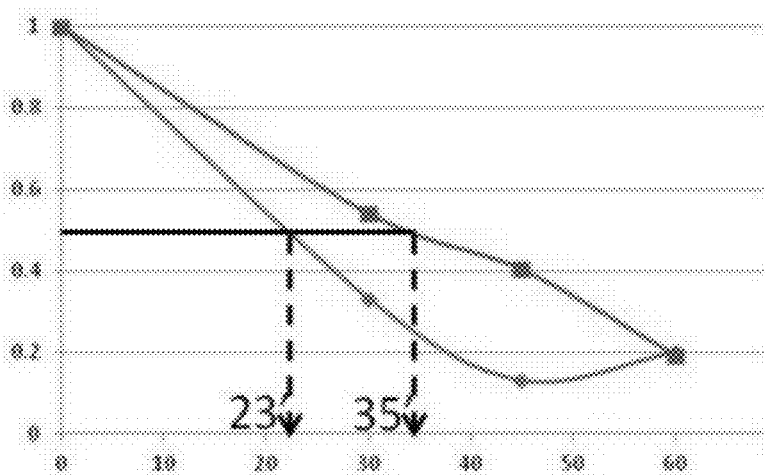
Figure 5A:
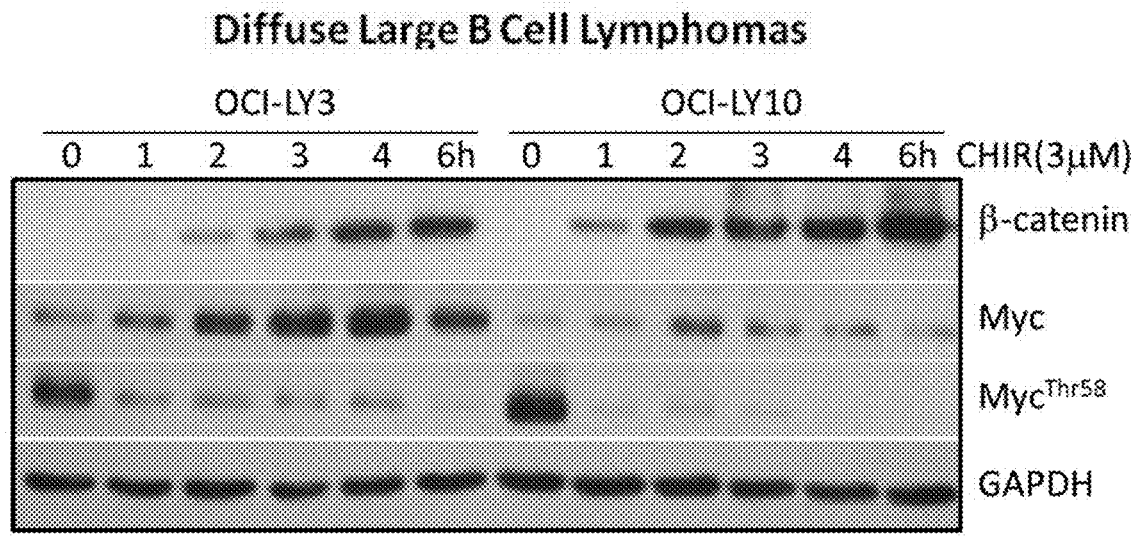
FIGS. 5A-5B: Inhibition of GSK3β transiently increases Myc levels in a variety of B cell malignancies: DLBCL (FIG. 5A) and Burkitt's Lymphoma (FIG. 5B).
Figure 5B:
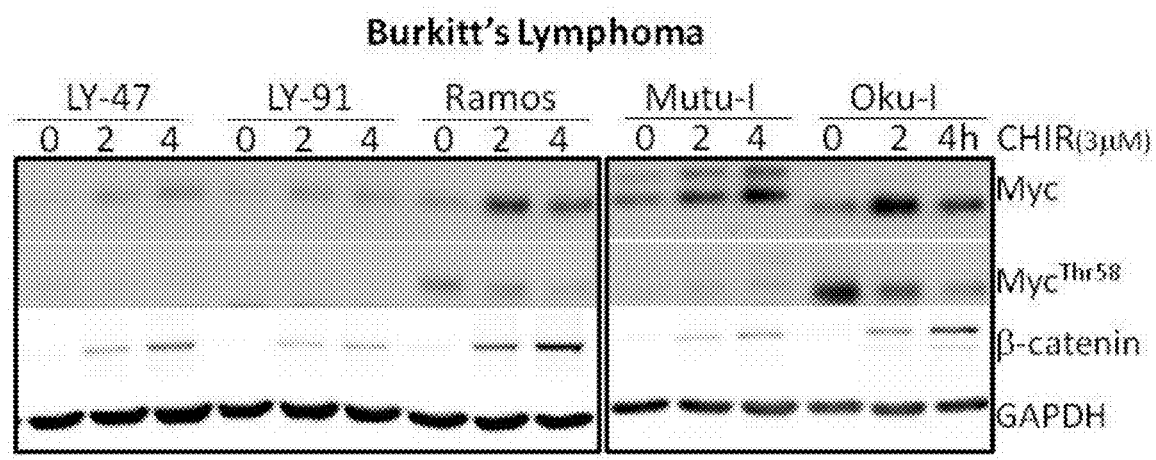
Figure 6A:
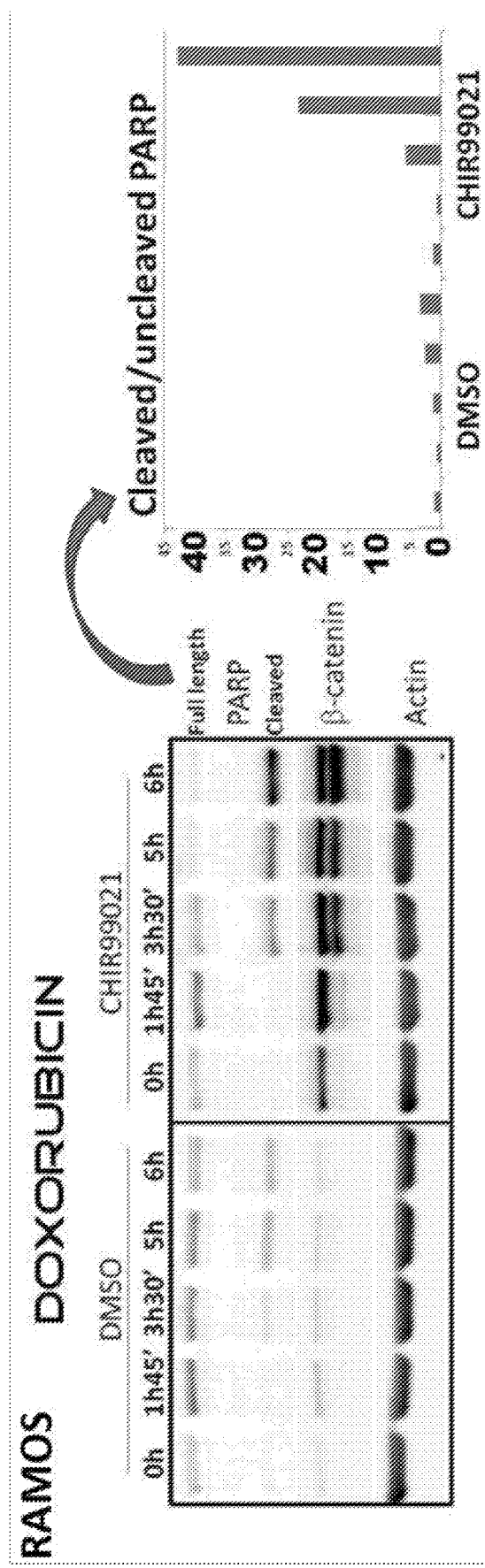
FIGS. 6A-6C: Inhibition of GSK3β results in increased apoptotic response of human Burkitt's Lymphoma cell lines to chemotherapeutic drugs.
Figure 6B:
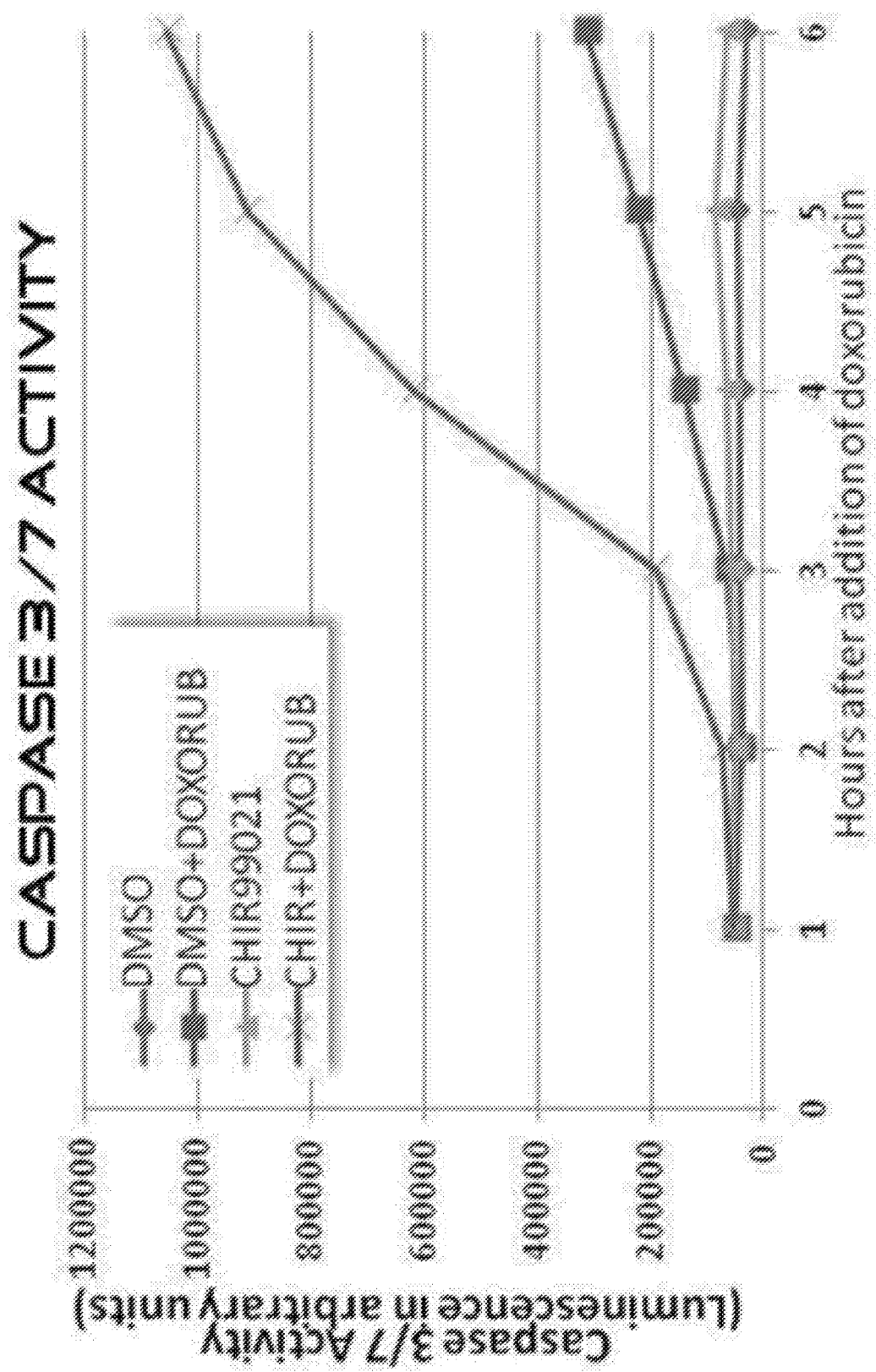
Figure 6C:
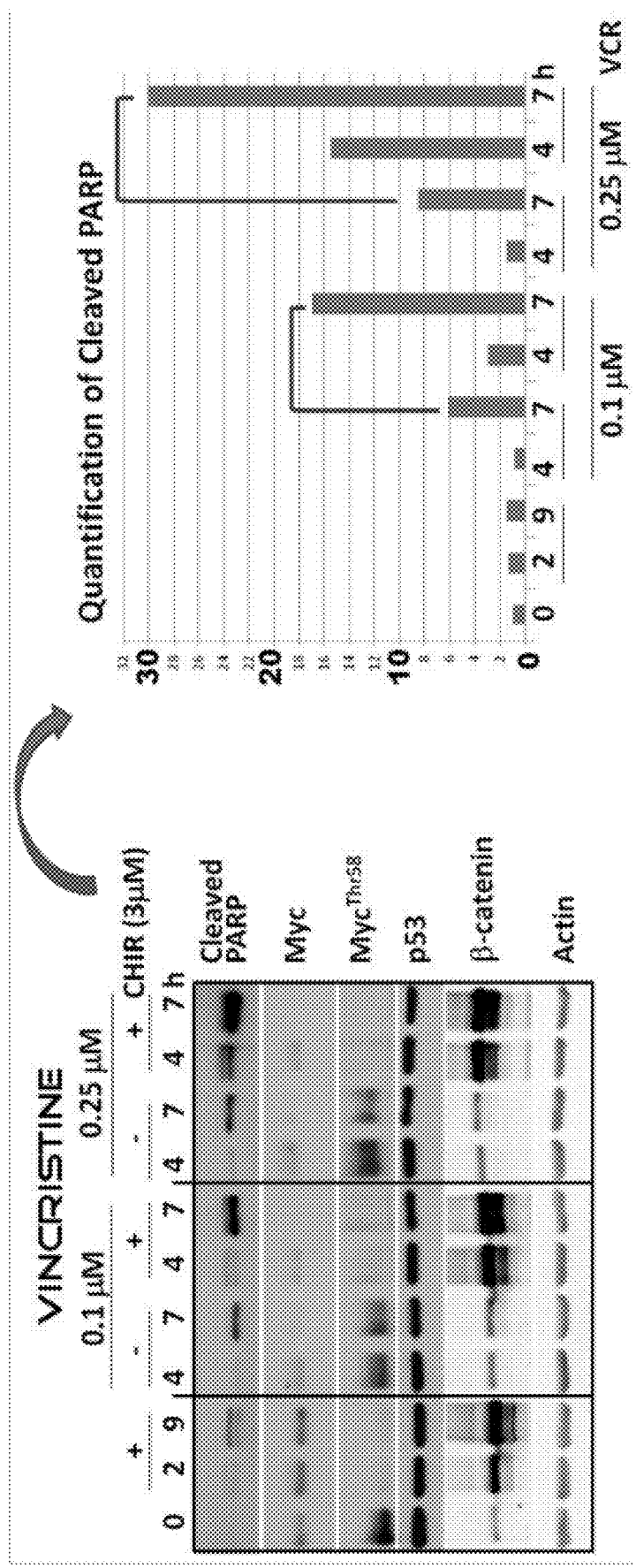

Because many Myc-driven tumors are defective for p53 activity, we sought to determine whether transient up-regulation of Myc also increases cell death in response to chemotherapeutic drugs in a p53-deficient background. For this purpose, we used B-lymphoma cells isolated from bone marrows of p53ER™ knock-in mice and subsequently transduced with a Myc-expressing retrovirus (2,3). See FIGS. 1A-1D. This inducible system allowed us to distinguish between p53-dependent (cells treated with tamoxifen) and independent (no tamoxifen added) cell death. Additionally, instead of modulating Myc levels through miRNA inhibitors, which currently have limited clinical utility, we increased Myc stability with a small molecule inhibitor of GSK3β, which promotes proteosomal degradation of Myc. See FIGS. 2A-2C. We observed that the activation of p53 via the addition of tamoxifen is sufficient to induce robust apoptosis, with neither modulation of Myc levels nor additional treatment with doxorubicin being necessary. On the other hand, in the absence of active p53, doxorubicin was needed to kill Myc/p53ER™ cells, but cell killing was rather inefficient. See FIGS. 3A and 3B. Remarkably, pharmacological stabilization of Myc strongly enhanced p53-independent doxorubicin-induced apoptosis. This enhancement was accompanied by selective activation of pro-apoptotic genes BIM, BAX and BAK, but not PUMA or NOXA, suggesting that the response was indeed p53-independent. See FIG. 3B. To validate this effect in a more relevant setting, we inhibited GSK3β in various Burkitt's lymphoma cell lines and achieved consistent up-regulation of Myc. See FIGS. 4A-4F. Most importantly, even in p53mut Ramos cells, Myc stabilization resulted in sharply increased responses to doxorubicin. See FIGS. 5 and 6. Our results suggest that transient up-regulation of Myc could be a viable adjuvant therapy even for tumors with p53 loss or MDM2 amplification.

Figure 7:
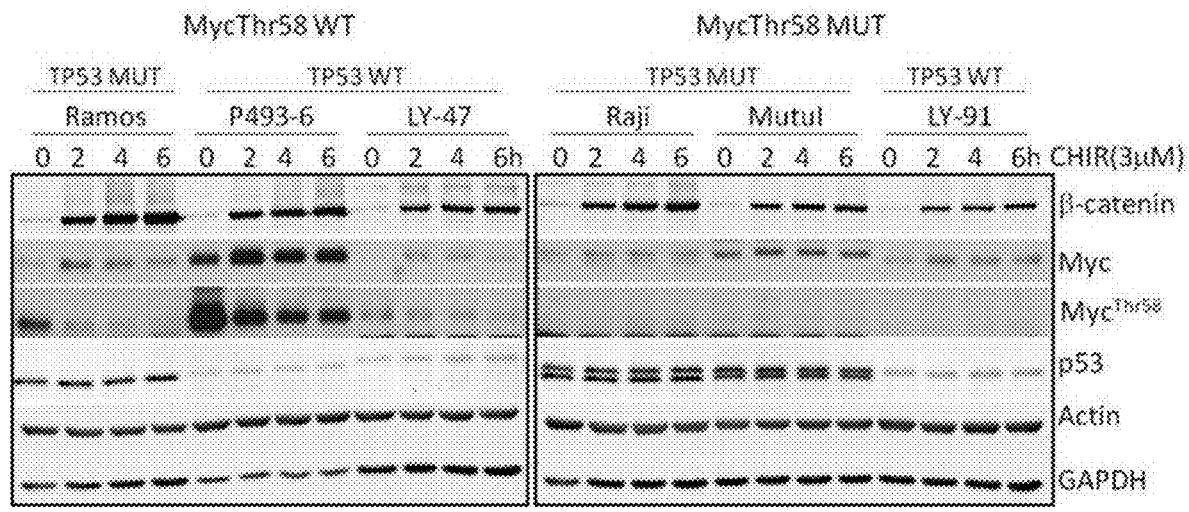
FIG. 7: Stabilization of Myc by GSK3-inhibitors requires retention of the Myc-Threonine 58 residue: B lymphoma cell lines with WT-Myc-Thr58 (left panel) or Mut-Myc-Thr58 (right panel) were treated with CHIR-99021 for indicated periods of time. CHIR-99021 induces stabilization of Myc only when the Myc-Thr-58 residue is retained (left panel).

As discussed above, treatment of Ramos cells [mutant for p53 and wild type for Myc (intact Threonine-58)] with GSK3-inhibitors increases the apoptotic response to drugs used to treat B cell lymphomas and leukemias within the CHOP-chemotherapeutic regimen: vincristine and doxorubicin. In our model, GSK3 inhibitors prevent phosphorylation of Myc at its Thr-58 residue by GSK3, inhibiting Myc degradation and inducing a transient stabilization and increase in the amount of the Myc protein. It has previously been shown that Myc-Thr58 is a hot spot for mutations in Burkitt's Lymphoma (Smith-Sorensen et al, JBC 1996), and when Myc-Thr58 is altered, the effect of transient stabilization induced by GSK3-inhibitors is lost (FIG. 7). Thus, cooperation of GSK3-inhibitors and chemotherapeutic drugs require retention of the Myc-Threonine-58 residue. This indicates that Thr-58 can be used as a predictive biomarker to identify those patients that will benefit from GSK3 inhibitor combined therapies.

Figure 8:
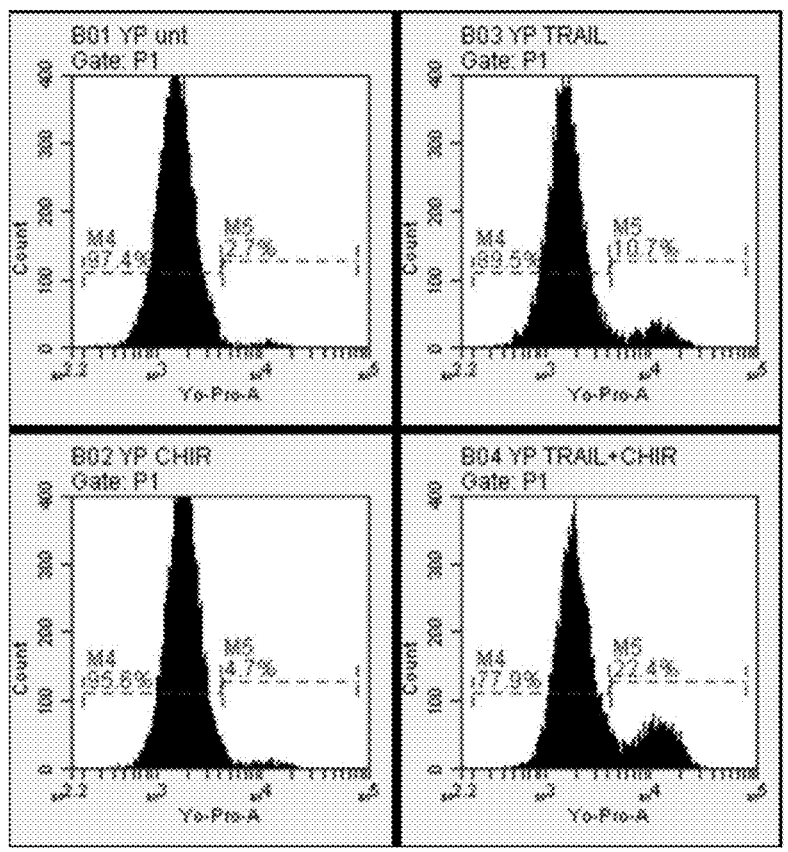
FIG. 8: Pretreatment of Ramos cells with CHIR-99021 increases the apoptotic response to TRAIL. Ramos cells where left untreated (top-left panel), treated with TRAIL for 5 h (top-right panel), treated with CHIR99021 alone (bottom-left panel) or pre-treated with CHIR99021 for 2 hours followed by 5 h of TRAIL (bottom-right panel). Percentage of death cells was measured by incorporation of the nuclear staining Yo-Pro. Percentages of living and apoptotic cells are shown in the M4 and M5 gates respectively.

Additionally, we have present new evidence showing that GSK3-inhibitors also increase cell death induced by the tumor necrosis factor (TNF)-related apoptosis-inducing ligand or TRAIL, as evidenced by flow cytometry analysis of Ramos cells using the nuclear localization of Yo-Pro (FIG. 8). TRAIL engages the extrinsic apoptotic pathway, activating Caspase-8, and is currently in clinical trials for the treatment of different oncological malignancies (reviewed in Stuckey and Shah, Trends in Mol Med 2013).

Figure 9A:
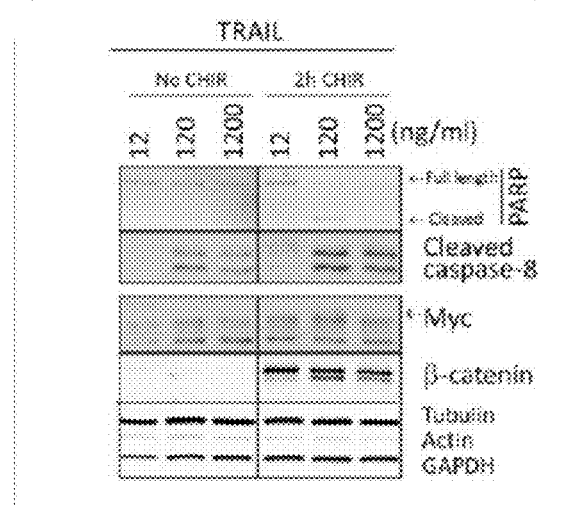
FIGS. 9A and 9B: Treatment of Raji cells with CHIR-99021 increases the apoptotic response to TRAIL. Raji cells were treated with indicated concentrations of TRAIL for 16 h in the presence or absence of CHIR-99021.
Figure 9B:
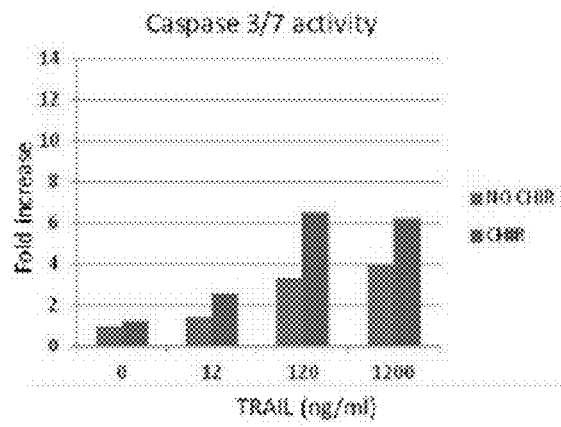

Surprisingly, treatment with TRAIL and CHIR-99021 not only induced cell death in cells with wild type Myc-Thr58 residue, but it also killed Raji cells, which have no functional p53 AND mutant Myc-thr58. This finding is relevant since, as mentioned above, Threonine-58 is a hot spot for mutations in Burkitt's lymphoma (Smith-Sorensen et al, JBC 1996). As shown in FIGS. 9A and 9B, there is an increase in the amount of cleaved caspase 8 and cleaved PARP detected by immunoblotting in Raji cells that are pre-treated with CHIR-99021 followed by TRAIL when compared to those treated only with TRAIL. The persistence of the effect of CHIR-99021 is evidenced by the increased levels of beta-catenin while the levels of mutant Myc remain constant, as expected. To perform a more quantitative assay, we also measured caspase 3 activity in Raji cells treated with increasing concentrations of TRAIL in the presence or absence of CHIR-99021, and consistently detected higher levels of caspase-3 activity in the latter (FIG. 9B).

While the use of the Chiron compound for enhancing p53 independent apoptosis is exemplified herein, there are a variety of GSK3β inhibitors available for use in the method of the present invention. These include the Chiron inhibitor CT99021((6-{2-[4-(2,4-dichlorophenyl)-5-(4-methyl-1H-imidazol-2-yl)-pyrimidin-2-ylamino]ethyl-amino}nicotinonitrile), lithium chloride, 6-bromoindirubin-3-oxime (BIO)(Calbiochem), 1-azakenpaullone (Calbiochem), AR-A014418, and SB216763. Any of these agents can be combined with other conventional anti-cancer agents to stabilize myc levels, thereby enhancing apoptosis in targeted cancer cells.

REFERENCES (1) Sotillo et al, Oncogene 2010
(2) Amaravadi et al, J Clin Inv 2007
(3) Yu et al, Blood 2007.
(4) Mussman et al. J. of Biol. Chem 282:12030-12037 (2007)
(5) Stuckey D W & Shah K. TRAIL on trial: preclinical advances in cancer therapy. Trends Mol Med. 2013, 19:685-94.
(6) Smith-Sørensen B, Hijmans E M, Beijersbergen R L, Bernards R. Functional analysis of Burkitt's lymphoma mutant c-Myc proteins. J Biol Chem. 1996, 27:5513-8.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for the treatment of B cell lymphoma in a patient in need thereof, comprising administration of an effective amount of CT99021((6-{2-[4-(2,4-dichlorophenyl)-5-(4-methyl-1H-imidazol-2-yl)-pyrimidin-2-ylamino]ethyl-amino}nicotinonitrile) in combination with a p53 independent apoptosis-inducing chemotherapeutic agent, said inhibitor being effective to inhibit Myc threonine 58 phosphorylation and stabilize Myc in a lymphoma cell, wherein the chemotherapeutic agent is selected from doxorubicin and vincristine, said combination acting synergistically to kill B cell lymphoma cells.

2. A method for the treatment of Burkitt's lymphoma in a patient in need thereof, comprising administration of an effective amount of CT99021((6-{2-[4-(2,4-dichlorophenyl)-5-(4-methyl-1H-imidazol-2-yl)-pyrimidin-2-ylamino]ethyl-amino}nicotinonitrile) in combination with doxorubicin or vincristine, said combination acting synergistically to kill Burkitt's lymphoma cells.

3. A method for the treatment of lymphoma in a patient in need thereof, comprising
    a) identifying a patient possessing a Threonine amino acid residue at position 58 of Myc; and
    b) administering a p53-independent apoptosis-inducing chemotherapeutic agent and a glycogen synthase kinase 3β (GSK3β) inhibitor to the patient of a) in an amount effective to induce B cell lymphoma cell death in said patient, wherein said GSK3β inhibitor is CT99021 ((6-{2-[4-(2,4-dichlorophenyl)-5-(4-methyl-1H-imidazol-2-yl)-pyrimidin-2-ylamino]ethyl-amino}nicotinonitrile) and said chemotherapeutic agent is doxorubicin or vincristine.

4. The method of claim 3, wherein the lymphoma is p53-defective.

5. The method of claim 1, wherein the B cell lymphoma is p53-defective.

6. The method of claim 3, wherein administrating the amount of the GSK3β inhibitor alone does not induce lymphoma cell death in said patient.

* * * * *